(12) United States Patent
Bondar

(10) Patent No.: US 8,734,155 B2
(45) Date of Patent: May 27, 2014

(54) DENTAL IMPLANT SYSTEM AND METHOD

(71) Applicant: Vitali Bondar, Portsmouth, NH (US)

(72) Inventor: Vitali Bondar, Portsmouth, NH (US)

(73) Assignee: Vitali Bondar, Portsmouth, NH (US)

( * ) Notice: Subject to any disclaimer, the term of this patent is extended or adjusted under 35 U.S.C. 154(b) by 0 days.

(21) Appl. No.: 13/900,888

(22) Filed: May 23, 2013

(65) Prior Publication Data

US 2013/0260336 A1 Oct. 3, 2013

Related U.S. Application Data

(63) Continuation of application No. 12/092,900, filed as application No. PCT/US2007/074847 on Jul. 31, 2007, now Pat. No. 8,469,710, and a continuation-in-part of application No. 11/615,131, filed on Dec. 22, 2006, now abandoned, said application No. PCT/US2007/074847 is a continuation of application No. 11/737,687, filed on Apr. 19, 2007, now abandoned.

(60) Provisional application No. 60/834,891, filed on Aug. 1, 2006.

(51) Int. Cl.
*A61C 8/00* (2006.01)

(52) U.S. Cl.
USPC .......................................... 433/172; 433/141

(58) Field of Classification Search
USPC ........................................... 433/172–176, 141
See application file for complete search history.

(56) References Cited

U.S. PATENT DOCUMENTS

| 5,584,629 | A  | * | 12/1996 | Bailey et al. | 411/178 |
| 6,168,436 | B1 | * | 1/2001 | O'Brien | 433/173 |
| 6,726,481 | B1 | * | 4/2004 | Zickmann et al. | 433/173 |
| 2004/0063069 | A1 | * | 4/2004 | Lombardi | 433/173 |

FOREIGN PATENT DOCUMENTS

WO  WO 9952466 A1 * 10/1999

* cited by examiner

*Primary Examiner* — Todd Manahan
*Assistant Examiner* — Michael R Ballinger
(74) *Attorney, Agent, or Firm* — Notaro, Michalos & Zaccaria P.C.

(57) ABSTRACT

A dental implant system including a dental implant having an apical end, a top end, an anchoring portion adjacent the apical end. The dental implant is adapted to engage bone and has an axial length. The dental implant has an internally threaded opening of a predetermined depth accessible from the top end of the dental implant. The system includes an abutment receiving portion adjacent the top end for receiving an abutment. The system also includes an annular shoulder formed between the anchoring portion and the abutment receiving portion. The system also has an implant abutment having a peripheral wall and a central axial bore extending through the abutment.

4 Claims, 11 Drawing Sheets

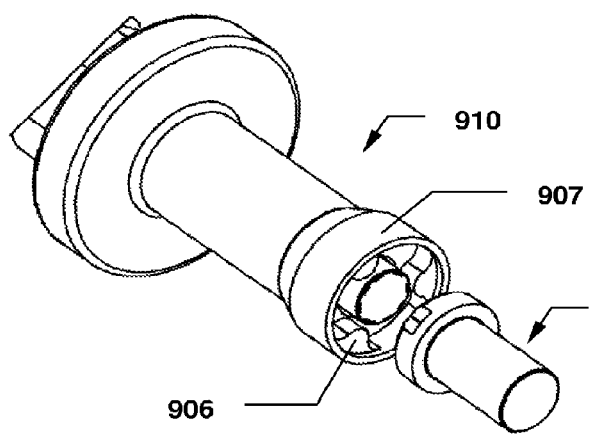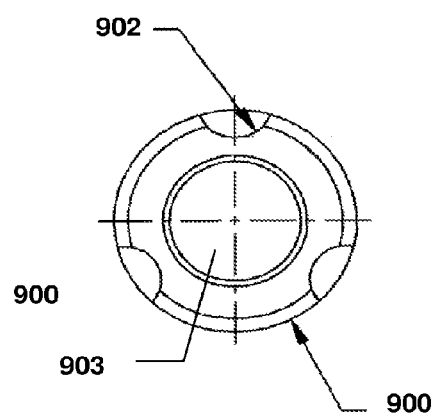
Fig. 19A　　　　　　　　　　　　Fig. 19B
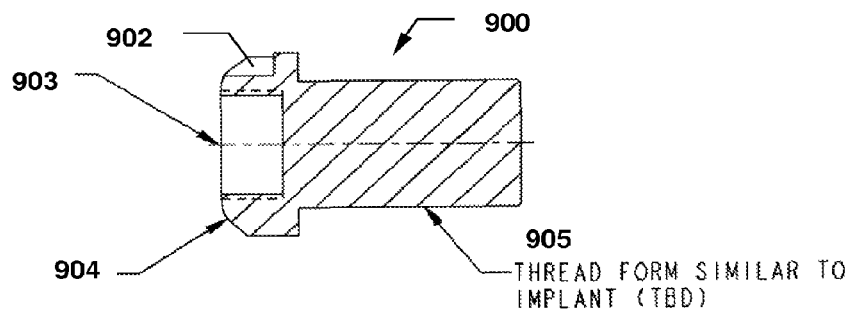
Fig. 19C

DENTAL IMPLANT SYSTEM AND METHOD

CROSS REFERENCE TO RELATED PATENT APPLICATIONS

This application is a continuation of U.S. Ser. No. 12/092,900, now U.S. Pat. No. 8,469,710, which is a continuation-in-part of U.S. Ser. No. 11/615,131, now abandoned, filed Dec. 22, 2006 and U.S. Ser. No. 11/737,687, now abandoned, filed Apr. 19, 2007, and claims benefit of U.S. Ser. No. 60/834,891, filed Aug. 1, 2006. The preceding applications are incorporated herein by reference in their entireties.

FIELD AND BACKGROUND OF THE INVENTION

The present invention relates in general to a dental implant system comprising components having improved surface and structural features for ensuring proper alignment and orientation of an abutment assembled on an implant and for preparing an accurate dental impression and mold representing the implantation site and its relationship to adjacent teeth structures. The present invention also relates to an implant having improved bone engaging surfaces for enhancing implant stability and fixation. The present invention further relates to a multi-component dental implant system with at least the implant and the abutment being detachably joined to one another with an improved, locking taper assembly designed for easy assembly and disassembly. The present invention further relates to an improved O-ring abutment assembly which offers a smaller footprint than existing O-ring attachment systems. The present invention further relates to an implant delivery method and its associated device(s) which reduces or eliminates, for example, slippage of the implant during implant surgery. The present invention further relates to a surgical screw delivery method and its associated device(s) which reduces or eliminates, for example, slippage of the surgical screw during surgery.

Abutment-to-Implant Connections

Internal Morse taper connection, also referred to as the locking taper, is known in implant dentistry and is commonly used for securing an abutment to a dental implant. A widely used example is embodied in the implant described in U.S. Pat. No. 4,738,623 to Driskell. See also U.S. Pat. No. 5,888,066 to Morgan and U.S. Pat. No. 6,290,500 to Morgan, et al. for examples of other Morse taper abutment-to-implant connections.

Known implant systems utilizing screw-less internal Morse taper connections have inherent disadvantages when compared to more widely used screw retained, internal or external hex dental implants. These disadvantages include: (1) the round shape of the female and male components makes it difficult to register the position of the prepared implant abutment; (2) the implant abutment may not travel in a straight line when tapped into the implant; (3) the round shape of the female and male components makes it difficult to prevent rotation of the implant abutment once the final restoration is under stress; (4) the implant abutment may be over-inserted into the implant as compared to the implant analog; and (5) the implant abutment may not be inserted into the implant as far as it was inserted into the implant analog. Tolerances used in manufacturing process are not adequate for reproduction of abutment insertion distance over the implant analog and the implant. It can be demonstrated in the following example. Abutment and implant are connected according to manufacturer protocol. The overall height of the abutment/implant assembly is recorded. The same abutment is connected with an implant analog (or with a different implant) and the same measurement is taken again. The difference can be more than 100-200 microns. The cause of this discrepancy was investigated with the help of computer software. The largest diameter of the male component was 3.0 mm; the taper of both components was 3 degrees. It was shown that if the diameter of the male component is only 6 microns smaller than a reference diameter, the components will be over inserted by 100 microns. The discrepancy becomes smaller as the taper angle increases. For example, 11 degrees connection of similar diameter will exhibit 2-3 times less discrepancy. But the benefit of the locking taper connection will be lost.

Locking engagement between complementary tapered surfaces of the implant and the abutment can be achieved through a tapping or threading operation. Some patients may find the use of tapping action to seat the abutment onto the implant uncomfortable. As an alternative, a dental implant system which utilizes a threaded fastener to seat the abutment onto the implant may be used. One example of a screw-assisted abutment connection is described in U.S. Pat. No. 6,726,481, issued to Zickmann, et al. There, a dental implant system is provided with an abutment post having an external tapered cylindrical surface, a projection extending from the top end of the abutment post and an abutment having complementary internal surfaces adapted to mate with the external cylindrical surface and projection of the abutment post. It is understood that the projection tends to increase the total height of the implant, subjecting the implant to more healing disrupting stress from mastication and tongue movements. The projection also makes fabrication of angled abutments more difficult. Also, the abutment of the aforementioned patent cannot be easily removed or replaced without damaging the abutment, crown or opposing dentition. In addition, it would be difficult if not impossible for the abutment and implant hex surfaces to mate accurately and for the conical or Morse tapered connection to operate properly at the same time. For example, the highest tolerance achieved by the machining process is no less than 12 microns. The Morse taper connection yields a 0.5 micron adaptation. In order to assure no interference with the Morse taper connection, the mating hex surfaces have to be manufactured to have significant tolerance to accommodate 12 microns margin of error for each mating surface. The gap between the external and internal hex must not be programmed to be less than 24 microns, but can be as large as 48 microns in the worst scenario. This would result in a significant rotational movement between the hexes during implant indexing and during abutment insertion. The error can be multiplied during the process of crown or bridge fabrication. The end result is most likely a restoration which does not fit properly.

Implant-Abutment Systems

One typical prior art system is described in U.S. Pat. No. 5,527,183, issued to O'Brien, which comprises an implant body having an externally threaded lower region and a plurality of tapered circumferentially extending members provided in an upper portion thereof.

The present invention also improves upon existing O-ring attachments. The basic concept of the O-ring type attachment is described in U.S. Pat. No. 5,049,072, issued to Lueschen. It consists of a metal housing, an O-ring, which is placed inside the housing, and an O-ring abutment, which is attached to the implant. The mechanism of retention is presented as follows:

the housing with the O-ring mounted therein is inserted over the spherical end of the abutment to detachably secure the housing to the abutment. The housing is designed to be encased within a denture or tooth (which can be natural or artificial). The O-ring must slip over the entire convexity of the spherical end in order to obtain good retention. Below the spherical end is a cylindrical spacer of a smaller cross-section, which needs to be of a certain length in order for the housing to have an appropriate range of movement. The housing includes a concave area on the inside wall adapted to receive the O-ring. This concave area needs to be sufficiently deep to incorporate most of the O-ring in order for O-ring not to come loose during denture insertion and removal. These two factors dictate the width and the height of the housing, apart from the diameter of the spherical end and the cross-sectional diameter of the O-ring.

The size of the housing and O-ring abutment is critical because the available space inside the denture can be quite limited. Others have attempted to reduce the overall height of the dental attachment assembly by altering the curvature of spherical or ball-shaped end of the abutment. One example is the Brevis attachment manufactured by Bicon (http://www.bicon.com/tech/t_od01.html). While further reduction of the height and width can be accomplished by reducing the thickness of the O-ring and the diameter of the spherical end of the abutment, such modifications will lead to diminished retention capability.

U.S. Pat. No. 6,981,871, issued to Mullaly, et al., describes a combination of a male abutment, a retaining housing and a soft liner with retentive protrusions. For this type of dental attachment assembly, the range of motion is limited to the amount of "give" the liner has. The liner, which must have a certain thickness to achieve any significant range of motion, will increase the width and height of the housing. Also, the cost of manufacturing the liner is higher when compared to O-rings. Further examples of O-ring type attachments can be found in U.S. patent application publication Nos. US 2006/0269903 of Bulard et al. and US 2002/0177103 of Pelak, and in U.S. Pat. No. 4,681,542, issued to Baum. The type of attachment described in Baum works well in situations where multiple teeth or implants are used to support removable denture. On the contrary, if few teeth or implants are used, the semi-rigid connection, which allows slight movement only along the vertical axis of the attachment, will apply too much stress on supporting teeth or implants and can lead to their failure.

Implant Delivery Method and Devices

This invention further attempts to simplify implant placement procedures and improve patient safety during these procedures. It is desirable to store the implant in a sterile container, which would securely hold the implant in an upright position, ready to be removed from the container and placed into the patient's bone. The common practice is to utilize the implant carrier with larger than implant diameter to hold implant in a container. Implant carrier can have mechanical interlock or is frictionally fitted with container's side walls. Carriers typically protrude from the container and can be gripped with fingers to be transferred into the receiving site. In order to utilize the improved method of implant delivery, as described below, the implant's proximal end should not be obstructed.

There are several ways to transfer implant from a sterile container into the prepared or pre-drilled bone. Most of the methods involve the use of an implant carrier. Implant carrier can be attached to the implant with a retention screw or can be attached to it by means of mechanical interlocking. Since it is not possible to touch the implant, the operator grips the carrier with fingers, places the implant into the drilled socket, rotates the implant to achieve initial stability and then disengages the carrier. If the retentive screw is used to attach the carrier, it has to be unscrewed with a screw removal tool. Screw removal tool has to have sufficient height and diameter in order for operator to apply the required force. It is common for diameter to be 10-15 mm, while the height can be as much as 20 mm. Only two fingers of one hand are used to accomplish this task. If the work is done on upper back teeth, it is easily seen that the screw removal tool can slip out of fingers and end up being swallowed or inhaled by the patient. Having the tool of this size also requires a large space between the carrier and the opposing teeth. Implant insertion instrument is then placed into the implant's well and implant is inserted to the desirable depth. Thus, at least three instruments are used with unnecessary risk of the implant coming loose and falling out of socket before the implant is securely anchored to the bone. It is therefore desirable to have a single, dual- or multi-use instrument which can be utilized by the surgeon to handle and manipulate the implant.

Surgical Screw and Driver

The invention attempts to simplify surgical screw placement procedures and improve patient safety during these procedures.

Current surgical screws, used to attach bone to bone or soft tissue to bone, have a head and a threaded portion. The head has retentive elements which allow the driver to apply rotational force necessary to place the screw into the bone. Secure connection between the screw and a driver is needed to assure safety of the operator and the patient. While a frictional fit is often provided between the driver tip and the recessed elements of the screw head, it is necessary to provide a definite connection which would resist off angle forces.

All cited references are incorporated herein by reference in their entireties.

SUMMARY OF THE INVENTION

One aim of the present invention is to provide a dental implant system and method which is capable of eliminating the disadvantages of the prior art and in particular a dental implant system which has surface and structural features which provide accurate placement of the abutment and replication of the implantation site.

It is an object of the present invention to provide a dental implant system comprising an implant member (or body), an abutment member (e.g., healing abutment or implant abutment), a transfer coping and a key.

The implant member generally has an anchoring portion on one end for anchoring the implant member in the patient's jaw bone, and an abutment receiving portion or post provided on the other end. At least a part or portion, or a cross-section, of the abutment receiving portion is tapered to a smaller diameter toward the top end of the abutment receiving portion. The abutment receiving portion has one or more spaced apart longitudinal grooves which extend downward from the top end thereof.

The key generally comprises one or more projecting members or projections, which extend axially outward from one end of the key. The projection(s) are arranged and configured to detachably mate with the corresponding groove(s) of the abutment receiving portion. The key also includes an elongated rail member formed on its circumferential or peripheral surface and extending substantially its entire length, or a portion thereof.

The abutment member generally includes an axial bore formed therein along its long or central axis. The lower portion of the axial bore has a tapered cross-section, configured to receive and mate with the tapered part of the abutment receiving portion. The upper portion of the axial bore has a cross-section corresponding to the outer cross-section of the transfer key.

Another object of the present invention is to provide an improved method of impression making and dental reconstruction utilizing the components of the dental implant system of the present invention.

Another object of the present invention is to provide a dental implant (member) comprising an apical end, a top end, an anchoring portion adapted to engage bone and having an axial length, an abutment or prosthesis receiving portion, an externally threaded region extending upwardly from about the apical end of the dental implant and comprising about 50% to about 95% of the axial length of the anchoring portion, and at least one annular, implant-stabilizing member formed between the threaded region and abutment receiving portion and comprising about 5% to about 50% of the axial length of the anchoring portion, wherein the implant-stabilizing member and the threaded region together making up no more than about 100% of the axial length of the anchoring portion. Preferably, the anchoring portion comprises at least two implant-stabilizing members disposed in parallel, spaced apart relation, and the implant-stabilizing members have successively smaller cross sections in the direction of the apical end of the dental implant to allow for bone condensing and gradual expansion during implant placement. The dental implants disclosed in U.S. Pat. No. 5,061,181 to Niznick and U.S. Pat. No. 4,468,200 to Munch required the bore that is formed in the patient's jawbone to have a larger upper section to accommodate the circumferential projections and a smaller diameter bottom section for thread engagement. Therefore, the implants of the above mentioned patents cannot be self-threading implants because of the difference in diameter between the receiving bore and the outside diameter of the circumferential projections. The object of this invention is to provide a self-threading internal or external connection implant capable of bone expansion during implant placement, to shorten the drilling time, to provide a better quality of bone around the implant and provide a better distribution of stress after implant loading.

Another object of the present invention is to provide a dental implant comprising an apical end, a top end, an anchoring portion adapted to engage bone and having an axial length, an abutment receiving portion having at least one spaced apart, longitudinal groove extending downwardly a predetermined length from the top end of the dental implant, and an internally threaded opening of a predetermined depth accessible from the top end of the dental implant. The dental implant may optionally include an annular shoulder formed between the anchoring portion and the abutment receiving portion, for example, when the diameter of the anchoring portion is greater than the diameter of the abutment receiving portion. If the diameter of the anchoring portion and the abutment receiving portion are approximately equal, then a shoulder is preferably not provided. Further, if the diameter of the anchoring portion is smaller than the diameter of the abutment receiving portion, then a "negative shoulder" may be incorporated into the anchoring portion.

Another object of the present invention is to provide a key for use with a dental implant of the present invention. The key includes an outer wall, a threaded axial bore, at least one longitudinal protrusion, a first pin receiving opening, at least one axial projection extending outwardly from one end thereof and adapted to detachably mate with the corresponding longitudinal groove of the abutment receiving portion, wherein the longitudinal protrusion and the first pin receiving opening are formed on the outer wall of the key. In an embodiment, the internally threaded opening of the dental implant has a smaller diameter than the threaded axial bore of the key.

Another object of the present invention is to provide an implant abutment (or member) for use with a dental implant of the present invention. The implant abutment includes a peripheral wall, a central bore extending through the implant abutment and having a lower part and an upper part, a cylindrical interior wall formed on the upper part of the central bore, a conical interior wall formed on the lower part of the central bore, a longitudinal channel formed on the cylindrical interior wall of the central bore and adapted to slidably mate with the longitudinal protrusion of the key, and a second pin receiving opening formed on the peripheral wall, wherein the cylindrical interior wall is adapted to receive in a fittingly close relationship the key, and wherein the conical interior wall is adapted to mate with the abutment receiving portion of the dental implant. The first and second pin receiving openings are adapted to be in alignment after the key and the implant abutment are properly seated on the dental implant. This allows the use of the pin to connect the key and the implant abutment, and permits the key and the implant abutment to be disengaged from the dental implant in a single operation.

Another object of the present invention is to provide a dental implant system comprising a dental implant and an implant abutment. The dental implant includes a top end, an anchoring portion adapted to engage bone, an abutment receiving portion having an external cylindrical surface which tapers toward the top end of the dental implant, and an internally threaded opening of a predetermined depth accessible from the top end of the dental implant. The implant abutment includes a lower part having an internal cylindrical surface which tapers outwardly toward a bottom end of the implant abutment, the internal cylindrical surface being adapted for secure mating engagement with the external cylindrical surface of the abutment receiving portion, and an upper part in communication with the lower part and having a threaded axial bore with a diameter larger than the internally threaded opening.

Another object of the present invention is to provide a method for obtaining an accurate translation of an orientation and position of an implant, which comprises providing an implant having a two or more spaced apart longitudinal grooves formed on an upper peripheral wall thereof, providing a threaded opening formed in an upper surface of the implant, providing an impression coping having axial projections corresponding to the longitudinal grooves of the implant and a threaded bore extending through the impression coping, seating the impression coping onto the implant, partially engaging the corresponding axial projections and longitudinal grooves, applying an axial force to the impressing coping with a fastener to urge the axial projections and the longitudinal grooves into a closely fitted engagement, applying a dental impression material to at least an area adjacent the impression coping so as to cover the impression coping to obtain an negative impression of said area, removing the fastener and then the impression material from the patient's mouth after the impression material has set, with the impression coping embedded in the impression material, detachably attaching the implant analog and the impression coping, pouring molding material into the negative impression formed in the impression material to form a dental cast model, and fabricating an implant abutment and/or dental prosthesis on the implant analog, wherein the fastener is adapted to cooperatively engage the threaded opening. Each longitudinal groove preferably has a larger cross section proximal portion, an apical portion having a smaller cross section than the proximal portion and a transition portion tapering between the proximal portion and the apical portion. In an embodiment, each proximal portion is adapted to freely receive the corresponding one of the axial projections until the transition portion, and the axial projections have sharp edges and are configured to provide at least two points of intimately engaging contact between the axial projections and the longitudinal grooves with the sharp edges of the axial projections biting into walls of at least the transition and apical portions. Further, the impression coping is preferably formed of a suitable biocompatible material which permits the axial projections to expand slightly outward when properly fitted into the longitudinal grooves.

Another object of this invention is to provide a healing abutment, which would allow implant orientation record to be taken while it is secured over the implant.

Another object of this invention is to provide the coding system to significantly minimize the insertion distance discrepancy between components of the locking taper systems.

Another object of this invention is to provide a surgical screw and a driver with improved retention elements.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 19A shows a perspective view of a surgical screw and a screw placement instrument of the present invention; and FIGS. 19B and 19C are top plan and side cutaway view, respectively, of the surgical screw of FIG. 19A.

DESCRIPTION OF THE PREFERRED EMBODIMENTS

Figures 1, 2:
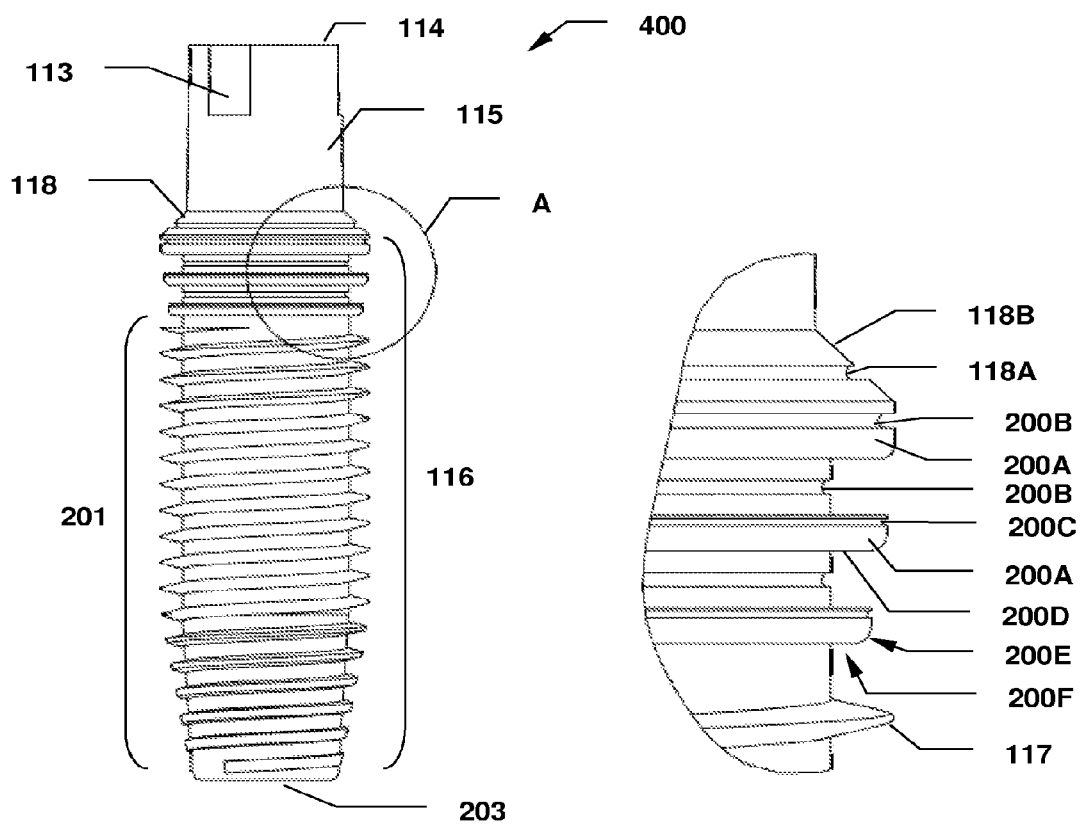
FIG. 1 is a side elevational view of an embodiment of a dental implant of the present invention.
FIG. 2 is close-up view of inset A of FIG. 1.

Referring now to the drawings, in which like reference numerals are used to refer to the same or similar elements, FIGS. 3-10 illustrate the dental implant system or assembly of the present invention, which comprises a dental implant 100, a key 102, an implant abutment 121, an abutment insertion tool 205, an abutment removal tool 206 and an implant insertion and removal tool 207.

Figure 3:
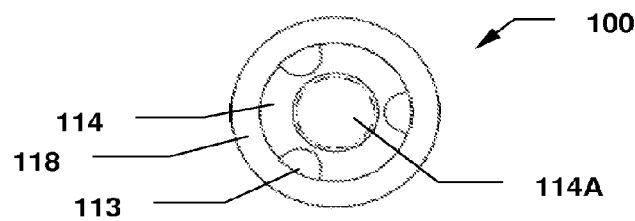
FIG. 3 is a top plan view of another embodiment of a dental implant of the present invention.
Figure 4:
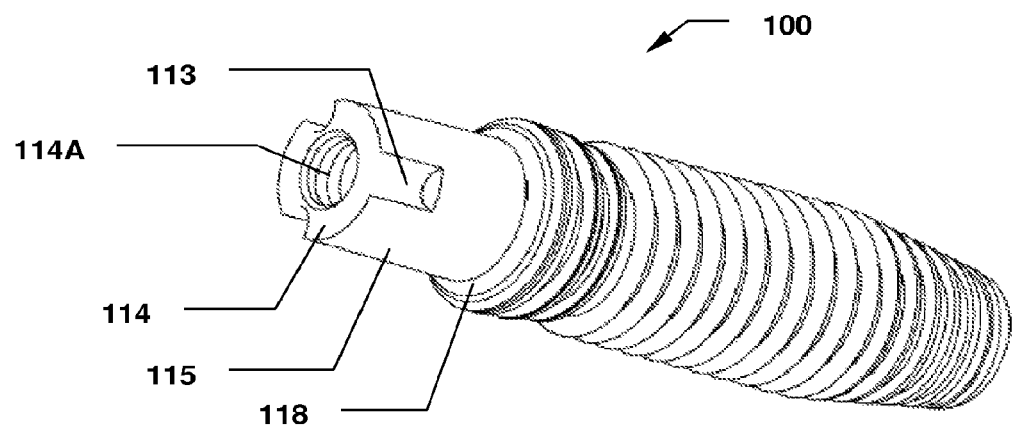
FIG. 4 is a perspective view of the dental implant of FIG. 3.

As shown in FIG. 4, the dental implant 100 is formed as an elongated body having an anchoring portion 116, an abutment receiving portion 115 and an internally threaded opening 114A of a predetermined depth, which is accessible from the top end 114 of the dental implant 100. The abutment receiving portion 115 can also be adapted to receive a prosthesis, such as a crown or a bridge, without the use of an abutment or the abutment being attached to it first. Preferably, the dental implant 100 has a cylindrical shaped body, and/or an annular shoulder 118 disposed between the anchoring portion 116 and the abutment receiving portion 115. The size and shape of the dental implant 100 may vary, depending on, for example, the surgeon's needs or preferences and/or the anatomical conditions present at the implant site. The abutment receiving portion 115 includes at least one longitudinal groove 113, and an external, conically tapered surface. Each longitudinal groove 113 is machined or formed (e.g., cast or molded) into the tapered surface of the abutment receiving portion 115, and preferably extends a predetermined distance from top end 114 toward the anchoring portion 116 of the implant 100. While the implant shown in FIGS. 3 and 4 is provided with three circumferentially equally spaced apart grooves 113, it will be appreciated that the number, shape, length, depth and arrangement of the longitudinal grooves 113 may vary, depending on the number, shape, length and arrangement of the axial projection(s) 107 of the key 102. Further, the inclination angle of the conically tapered surface is selected to form a taper connection, such as a Morse taper connection, with the conical interior wall in the conical bore section 110B (FIG. 5) of the abutment 121.

Generally, a Morse taper, also known in the art as locking taper or conical connection, is defined, in a non-limiting fashion, as a taper connection having a taper surface making an angle of about 1 to 12 degrees relative to the longitudinal axis of the component. Morse taper connections can be made between interpenetrating parts, with, e.g., a first of the parts having a tapered bore, and a second of the parts having a frusto-conical shape for securement in the tapered bore of the first part. The tapered bore and the frusto-conical shape can have slightly different sizes or taper angles to facilitate securement of the parts via the mating taper connection as described below. To assemble mating taper connections, including Morse taper connections, items having a mating taper structure are interference fit one to the other to cause co-integration or locking of the items. See, e.g., U.S. published application number US 2004/0111861 of Barrette, et al.

Figure 5:
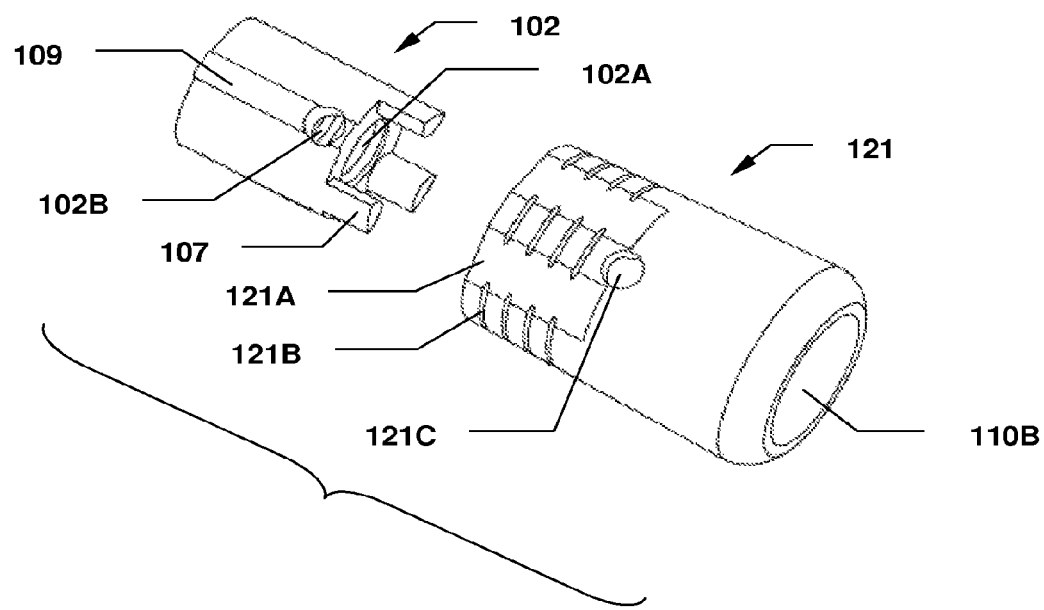
FIG. 5 is a perspective view of an embodiment of a key and implant abutment of the present invention.
Figures 6A, 6B:
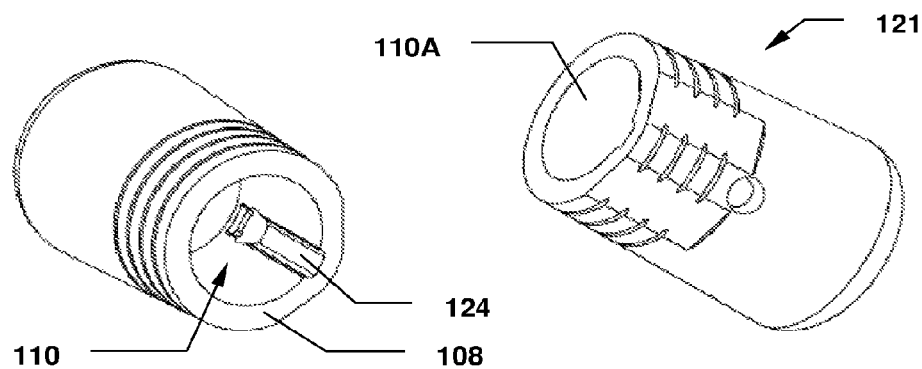
FIGS. 6A and 6B are two different perspective views of the implant abutment of FIG. 5.
Figure 7:
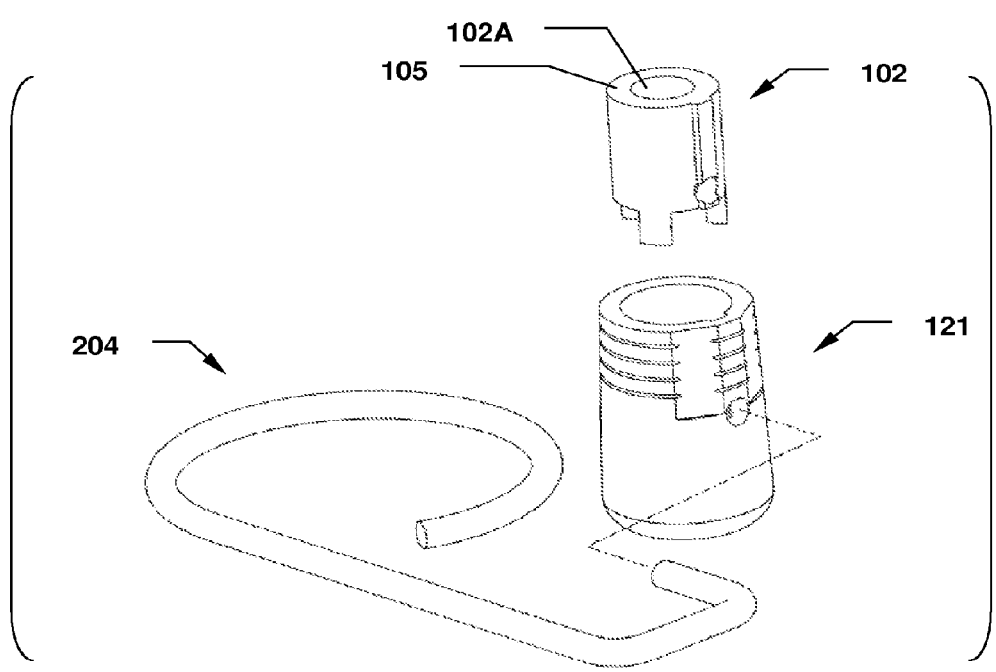
FIG. 7 is perspective view of a locking pin of the present invention and the key and implant abutment of FIG. 5.

As shown in FIG. 5, the key 102 has a cylindrical outer wall, a longitudinal protrusion 109 disposed along the entire length (or a portion) of the outer wall, a pin receiving opening 102B which can be a blind hole or a through-passage opening, a threaded axial bore 102A, and projections 107 which extend axially outward from one end of the key 102. The key 102 preferably has one or more circumferentially equally spaced projections 107 configured for detachable engagement with the corresponding number of correspondingly dimensioned longitudinal grooves 113 of the implant 100. It will be appreciated that the key 102 can also have more than one longitudinal protrusion 109 which can respectively mate with the corresponding longitudinal channels 124 in the implant abutment 121 (FIGS. 5-7). It will also be appreciated that the key can be provided without a longitudinal protrusion and a pin receiving opening, and that the abutment can be manufactured without corresponding longitudinal channel(s). In an embodiment, the key can be fitted and permanently attached inside the abutment.

As shown in FIGS. 5-7, the implant abutment 121 has an outer peripheral wall, a pin receiving opening 121C and a central bore 110. The central bore 110 is comprised of a cylindrical bore section 110A and a conical bore section 110B. The cylindrical bore section 110A has a cylindrical interior wall which is configured to receive in a fittingly close relationship the key 102. Formed on the cylindrical interior wall is at least one longitudinal channel 124 for sliding engagement with the longitudinal protrusion 109 and for guiding the insertion of the key 102 through cylindrical bore section 110A of the central bore 110. Although the key 102 and the cylindrical bore section 110A are shown as having a circular cross-section, it will be appreciated that they may have other suitable cross-sectional shapes. As described above, the abutment can be manufactured without a longitudinal channel if a permanent connection (press fit, welding) between the key and abutment is desired. Further, it will also be appreciated that the cross-sectional size and height of the key and the cylindrical bore section can be selectively varied by one skilled in the art as may be appropriate to improve the form-fitted engagement between the key and the cylindrical bore section of the implant abutment.

The outer peripheral wall of the implant abutment 121 may be optionally provided with anti-rotational elements. Although the outer peripheral wall of the implant abutment 121 is shown with flatten areas 121A and non-continuous, annular grooves 121B (see FIG. 5), it is contemplated that other suitable patterns of surface protuberances, recesses or treatments may be used.

In an embodiment, the abutment receiving portion 115, the implant abutment 121 and the key 102 are precisely machined or formed to at least provide approximate alignment for the pin receiving openings 102B, 121C when the implant abutment 121 and the key 102 are properly seated on the implant 100. Preferably, opening 102B does not penetrate through the cylindrical inner wall of the key 102.

The pin receiving openings 102B, 121C are used to releasably connect the key 102 and the implant abutment 121 with a locking pin, such as the one shown at reference numeral 204 in FIG. 7. By joining the implant abutment 121 and the key 102, they can be disengaged from the dental implant 100 with a single operation. This is usually sufficient to remove the abutment, unless the key and the abutment are joined together in which case the locking pin is not required. The pin receiving openings 102B, 121C may be positioned at any suitable location on peripheral wall of the implant abutment 121 and the key 102, provided that the openings do not interfere with the form-fitted engagement of the implant abutment 121, the key 102 and dental implant 100.

Figure 15:
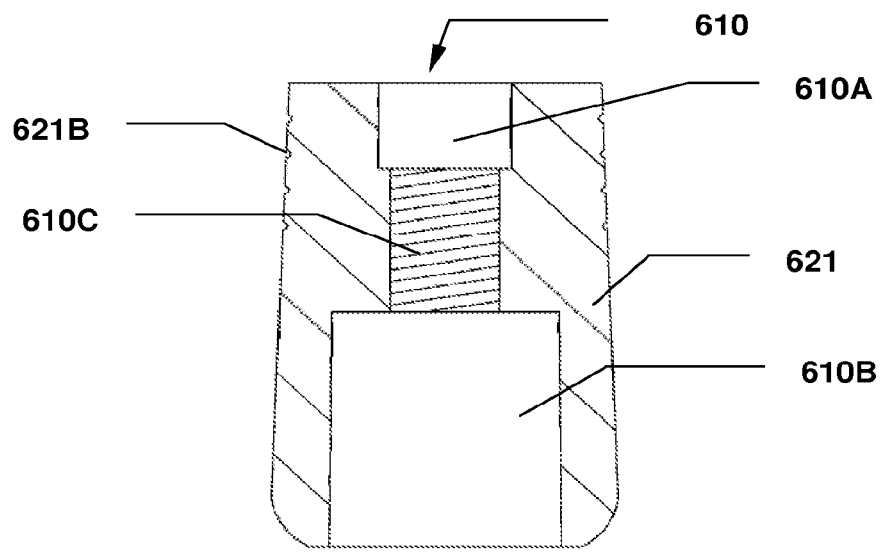
FIG. 15 is a side cut-away view of an implant abutment of the present invention.

Referring now to another embodiment of the implant abutment of the present invention which will be discussed with reference to FIG. 15, implant abutment 621 is provided with a central bore 610 which is comprised of a cylindrical bore section 610A, a threaded bore section 610C and a conical or tapered bore section 610B. Implant abutment 621 can be seated or removed from the abutment receiving portion of an implant using an abutment insertion and removal tool, respectively, in a manner as discussed below. The conical or tapered bore section 610B of the implant abutment 621 is configured to mate with a complementary tapered surface of the implant to preferably form a Morse taper connection. Bore section 610C has a larger diameter than bore 114A in the abutment receiving end 115 and is threaded to cooperatively engage with the threads on the abutment removal tool.

Figure 10:
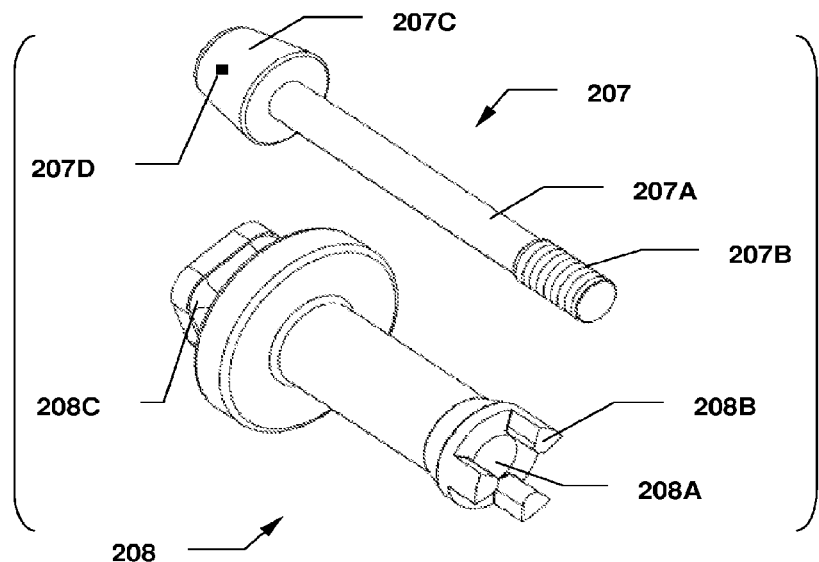
FIG. 10 is a perspective view of an implant placement tool of the present invention.
Figure 11A:
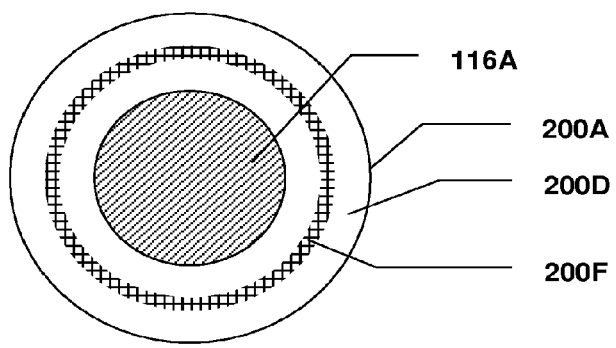
FIGS. 11A to 11D are bottom cut-away plan views of the implant-stabilizing members or fins with various bone ingrowth surfaces, openings or grooves.
Figure 11B:
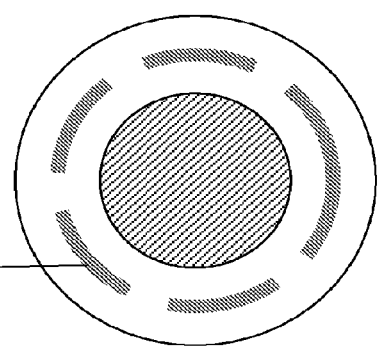
Figure 11C:
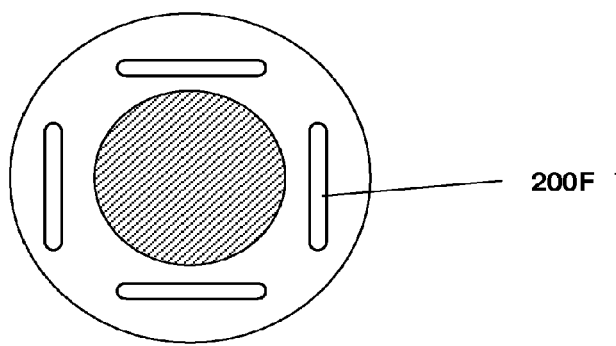
Figure 11D:
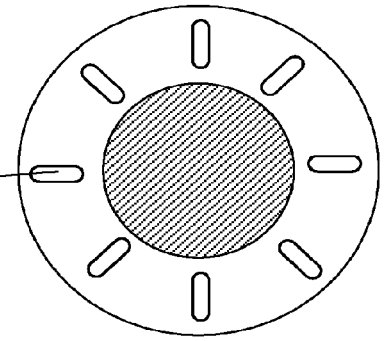

Installation of the alternate preferred dental implant system will be described below. First, a dental implant 100 made of a biocompatible material such as titanium alloy, pure titanium or ceramic is implanted into a patient's jawbone. Installation of the dental implant 100 may be performed with an implant placement instrument 208 as shown in FIG. 10. The lower end of the implant placement instrument 208 is provided with axially extending projections 208B, resembling those found on the transfer key 102, for engaging the longitudinal grooves 113 on the dental implant 100. The projections can be surrounded by an annular collar, if desired or necessary, to provide more rigidity. The upper end 208C of the implant placement instrument 208 may be formed with tool engagement surfaces or recesses for engagement with a torque applying tool, such as a torque wrench.

An opening 208A extends longitudinally through the implant placement instrument 208 and is configured to receive a threaded fastener 207 for threadedly securing the implant placement instrument 208 to the dental implant 100. The threaded fastener 207 has a rod shaped member 207A which is threaded at one end 207B for cooperatively engaging the threads of the internally threaded opening 114A of the dental implant 100. An enlarged head member 207C is formed at the other end of the rod shaped member 207A to provide a gripping surface for rotating the rod shaped member 207A. To form a tight connection between the implant placement instrument 208 and the implant, longitudinal grooves of the same size as grooves 113 can be placed in member 207C. A placement tool, similar to tool 208 can engage those grooves and rotate fastener 207. Alternatively, a hex or other shaped socket or retentive cavity can be placed on the top of member 207C. A through bore 207D may also be placed on the side of the member 207C and be used in conjunction with a pin. Since there is a limited amount of space available during the surgery, the use of the pin is advantageous for the following reasons: 1) pin has a much lower profile than traditional torque applying instruments; 2) it also allows for a significant torque to be applied without the use of a torque wrench.

The implant placement instrument 208 can be used to retrieve the implant from its storage container and thereafter carry the implant to the patient's mouth for insertion. This advantageously reduces the number of manipulative steps that need to be performed and the number of loose pieces that need handling during implant installation.

Figure 16:
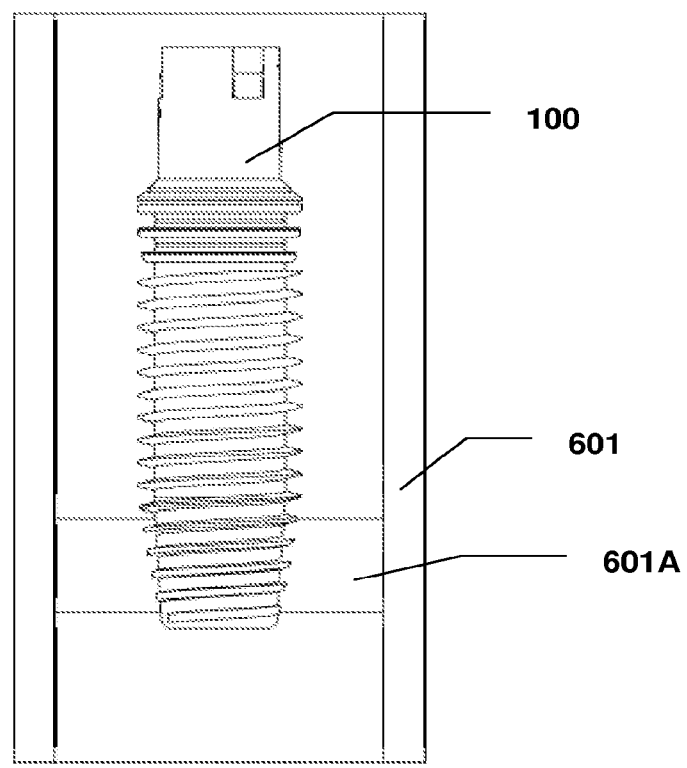
FIG. 16 is a side elevational view of an implant holding vial of the present invention with an implant retained by the implant retaining member.

Implants, generally designated as 100, may be individually stored in implant holding vials or open end sleeves, such as the vial shown at reference numeral 601 in FIG. 16. The vial is preferably made of a plastic material. The vial can have any suitable shape such as cylindrical, triangular, square, etc. An implant supporting member 601A, made of plastic, ceramic, pure titanium or titanium alloy, with a disk-, cylindrical-, square- or any suitably shaped body is placed inside the vial and preferably spaced above the bottom of the vial to keep the implant 100 from coming into contact with the sidewalls and the bottom of the vial. The implant supporting member 601A may include a threaded bore with the thread pitch and shape corresponding to that of the implant 100 for retaining the implant 100 in a substantially vertical orientation. The implant supporting member 601A may be adapted to either engage the thread of the implant or the implant stem or both. Alternatively, member 601A can have a conical internal chamber corresponding in size to the tapering end of the implant. This way, the implant 100 can be easily retrieved from the vial using, for example, the implant placement instrument 208. In another embodiment, the implant supporting member and the implant can be stored in a plastic pouch. The implant supporting member can have pins inserted into the bores, which are placed in each corner or equally or unequally spaced around the periphery of the implant supporting member. Pins can be sufficiently long and have a predetermined spacing in order for the implant not to come in contact with the pouch.

It will be appreciated that the implant insertion tool 208 is readily adaptable to serve as an implant removal tool.

After the implant is securely affixed to the patient's bone and sufficient healing has occurred, the crown or dental prosthesis, the key 102 and implant abutment 121 are then prepared according to the method of the present invention, as is disclosed herein.

The key 102 is inserted into the cylindrical bore section 110A of the implant abutment 121. In one embodiment, the key 102 and the implant abutment 121 are joined together into one piece in the manner as described herein above. Next, the implant abutment 121 is placed over the abutment receiving portion 115 and rotated to engage the corresponding projections 107 and longitudinal grooves 113.

Figure 8:
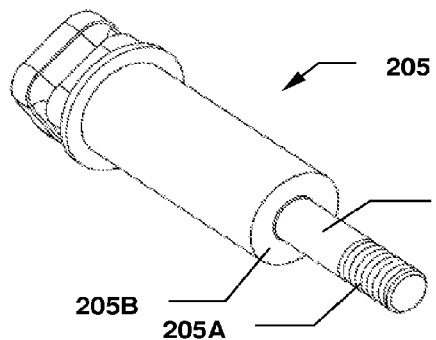
FIG. 8 is a perspective view of an abutment insertion tool of the present invention.
Figure 9:
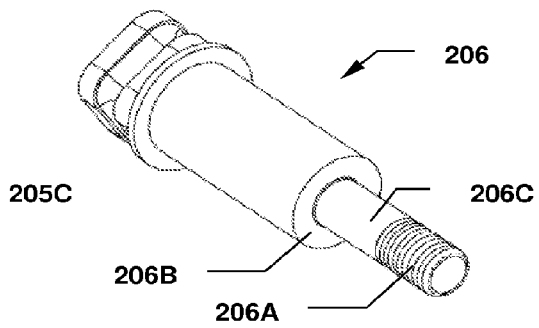
FIG. 9 is a perspective view of an abutment removal tool of the present invention.

After the implant abutment 121 is placed over the dental implant 100, namely over the abutment receiving portion 115, and the axial projections 107 are engaged with the longitudinal grooves 113, an abutment insertion tool, such as the one shown at reference numeral 205 in FIG. 8, is lowered through the axial bore 102A of the key 102. It is contemplated that the axial bore 102A forms a passage with a cross-section larger than that of the internally threaded opening 114A of the dental implant 100 so as not to interfere with the insertion and rotation of the abutment insertion tool 205.

Abutment insertion tool 205 is provided with a rod shaped member 205C having threads at one end 205A for cooperatively engaging the threads in the internally threaded opening 114A of the dental implant 100. The rod shaped member 205C extends outward from a flat surface 205B which is dimensioned to have a larger cross-section than the abutment opening 110A (see FIG. 6B) of the implant abutment 121.

By rotating the abutment insertion tool 205 in a thread engaging direction, an axial seating force is applied to urge the respective tapered surfaces of the implant abutment 121 and the abutment receiving portion 115 tightly together, preferably forming a Morse taper connection. The flat surface 205B of the abutment insertion tool 205 abuts and slidably rotates against the occlusal surface 108 of the implant abutment 121 as the abutment insertion tool 205 is turned into the internally threaded opening 114A by rotation against the threads in said opening. If the top of the abutment is shortened or if there is a large gap between occlusal surface 108 and flat surface 205B, a spacer of an appropriate thickness may be placed between the implant abutment 121 and the flat surface 205B of the abutment insertion tool 205. The key 102 registers the vertical position of the implant abutment 121, which ensures that the implant abutment 121 travels in a straight line during abutment seating. It will be appreciated that the height of the key 102 is proportional or related to the height of the implant abutment 121, and that the height of the key 102 should not interfere with the proper seating of the implant abutment 121. Further, the rotation of the abutment insertion tool 205 may be accomplished with a torque applying tool, such as a torque wrench, and the upper extremity of the abutment insertion tool 205 may be adapted to accept the torque applying tool.

After the implant abutment 121 is properly seated, the abutment insertion tool 205 is removed by rotation in a thread disengaging direction. Finally, the crown or dental prosthesis is fabricated and attached (e.g., cemented) over the implant abutment 121.

Abutment removal is accomplished as follows. A hole is placed on the occlusal surface of the crown or dental prosthesis to gain access to the axial bore 102A of the key 102. The threaded end 206A of the abutment removal tool 206 is threadedly directed into the axial bore 102A of the key. If the key 102 and the implant abutment 121 were separately mounted on the abutment receiving portion 115, the cement used to attach the crown or dental prosthesis to the implant abutment 121 will permeate into the pin receiving openings 102B, 121C and join the implant abutment 121 and the key 102 together. The combined implant abutment 121 and key 102 can be detached from the abutment receiving portion 115 by applying an axial and/or rotational force using the abutment removal tool 206.

Alternate Implant Anchoring Structure

The implants of the present invention may alternately employ a blade-type or a press-fit fixture. It will be appreciated that the size, shape and arrangement of the blade-type or a press fit fixture can vary.

A further embodiment of the invention is depicted in FIG. 1, which shows a dental implant 400 provided with an anchoring portion 116 having three annular, implant-stabilizing members 200A (or fins) and a threaded region 201. The number of implant-stabilizing members 200A may vary from one to three or more as desired, and preferably comprises about 5% to about 50% of the axial length of the anchoring portion 116. While the anchoring portion 116 has a generally cylindrical shape and is tapered at its lower extremity, other shapes or profiles (such as frusto-conical, conical and uniformly cylindrical profiles) of the anchoring portion may be used. Unless otherwise specified, it is to be understood that all of the components of the alternate embodiments are substantially the same as the other embodiments discussed above.

The threaded region 201 extends from about the apical end 203 toward the abutment receiving portion 115 of the dental implant 400 (see FIG. 1), and preferably comprises about 50% to about 95% of the axial length of the anchoring portion 116. The implant-stabilizing member(s) 200A is disposed between the threaded region 201 and the abutment receiving portion 115. The threads 117 (FIG. 2) in the threaded region 201 can be continuous or non-continuous and uniform or non-uniform, and the ends of the threads 117 can be flat or tapered. The continuity, uniformity, shape, pitch, depth, and spacing of the threads 117 may be varied to obtain the best holding power and screwing/cutting characteristics.

If the diameter of the abutment receiving portion 115 is smaller then the diameter of the anchoring portion 116, an annular shoulder 118 may be disposed between the anchoring portion 116 and the abutment receiving portion 115, and may optionally comprise a continuous or non-continuous, circumferentially extending groove 118A (see FIG. 2) formed on an annular surface 118B thereof. While the annular surface 118B is shown as having a downward slope, which forms an acute angle with the lower edge of the annular shoulder 118, it will be appreciated that the annular surface 118B can be oriented at about 90 degrees or at any suitable acute or obtuse angle relative to the lower edge of the annular shoulder 118. If the diameter of the abutment receiving portion 115 is greater than the diameter of the anchoring portion 116, which is likely to occur with transitional or mini-implants, then a "reversed" shoulder will be employed to generate the transition between the above-mentioned portions. If the diameters of the abutment receiving portion 115 and the anchoring portion 116 are approximately equal, then a cylindrical collar is provided between portion 115 and 116.

If two or more implant-stabilizing members 200A are employed, each successive member, toward the apical end of the implant, preferably has an incrementally smaller cross section than its preceding member. This allows for a gradual, wave-like bone expansion during implant insertion. Also, the width or diameter of the uppermost, implant-stabilizing member and the lower edge of the annular shoulder 118 and maximum diameter of the threads 117 of the threaded region 201 are preferably substantially equal to each other. In the non-limiting embodiment shown in FIG. 1, three implant-stabilizing members 200A are disposed on the dental implant 400 between the annular shoulder 118 and the threaded region 201 in generally parallel spaced apart relation. The number and arrangement of the implant-stabilizing member(s) may vary, depending on, for example, the surgeon's needs or preferences and/or the anatomical conditions present at the implant site.

If the uppermost, implant-stabilizing member is formed integrally with the annular shoulder 118 below its lower edge, an annular groove 200B is optionally provided between the uppermost, implant-stabilizing member and the annular shoulder 118. None or one or more implant-stabilizing members 200A may be provided with an annular groove 200C around the outer edge. Further, at least one annular groove may be provided on the axial wall of the anchoring portion below at least one implant-stabilizing member 200A or between at least one pair of neighboring, implant stabilizing members 200A. The depth and width of annular grooves 118A, 200C, 200B of the annular shoulder 118, the implant-stabilizing member(s) 200A and the axial wall of the anchoring portion 116, respectively, preferably ranges from about 0.01 mm to about 0.2 mm. It is contemplated that annular grooves 118A, 200C, 200B and the implant-stabilizing member 200A can have continuous or non-continuous surfaces or structures.

In one embodiment, the implant-stabilizing member 200A has a curved peripheral edge 200E which helps to displace or expand the bone tissue to facilitate passage of the implant-stabilizing members 200A into the bore hole in the patient's jaw bone. Preferably, axially, longitudinally, or circumferentially continuous or non-continuous ribs or grooves 200F or combinations thereof are formed on the apical surface 200D of the implant-stabilizing member 200A for promoting bone ingrowth (see FIGS. 11A-11D). FIGS. 11A-11D show cut-away views of the implant stem 116A and examples of different surface structures that can be employed in the apical surfaces 200D of the implant-stabilizing member 200A. The ribs or grooves 200F on the apical surface 200D may be formed to extend entirely through the implant-stabilizing member 200A. The ribs or grooves 200F can be either machined (e.g., laser cutting or engraving) or cast into the apical surface 200D.

O-Ring Abutment Assembly

In FIGS. 12A to 12F, another aspect of the present invention is illustrated. In this embodiment of the invention, an O-ring abutment assembly (which can also be an attachment for natural tooth), generally designated 530 and employed in removable denture, tooth (natural or artificial) or dental prosthesis, is provided with an O-ring 537, an abutment 503 and a retainer housing 535. The abutment 503 is comprised of a downwardly tapering seat member 532 having an upper end 532A and a lower end 532B, an anchoring portion 533 extending downwardly from the lower end 532B of the seat member 532, an upwardly extending spacing member 531 having one end connected to the upper end 532A of the seat member 532, a plate member 538 connected to the spacing member 531 opposite the seat member 532 and a having a plurality of peripherally-disposed axial grooves 513, and a circumferential cavity 536 defined by the upper end 532A of the seat member 532, the spacing member 531 and the plate member 538. The cavity 536 is configured to receive and releasably retain a major portion of the cross section the O-ring 537, preferably at least 70% of the cross-sectional area of the O-ring 537 is disposed within the cavity 536. In another preferred embodiment, at least 85% of the cross-sectional area of the O-ring 537 is disposed within the cavity 536. The abutment 503 may be formed (e.g., machined, cast or by other suitable means) as a single piece or as a plurality of permanently or detachably connected pieces.

The remaining peripheral portion of the O-ring 537 that extends beyond the peripheral edge 536A of the cavity 536 is operable to engage the circumferentially extending groove 535A formed on the interior cavity wall 535B of the retainer housing 535 to provide an interference fit between the abutment 503 and the retainer housing 535. Alternatively, instead of using the retainer housing 535 as an intermediate mounting collar, a groove, similar to groove 535A of FIG. 12F, can be provided on the interior cavity wall of an artificial tooth or denture and mounted directly on the abutment 503.

The amount (or the cross-sectional area) of the O-ring 537 received within the cavity 536 is selected to minimize the peripheral portion of the O-ring 537 that is received by groove 535A of the retainer housing 535, while providing an interference fit between the abutment 503 and retainer housing 535 that can withstand a desired minimum, axial pull-out force (or separation force). In this way, the overall cross-section of the abutment is reduced. A preferred reduced height of the abutment is achieved by selecting a minimum thickness for the plate member 538 for providing a desired mechanical stability. Preferably, the thickness of the plate member 538 is selected such that it does not deform under the stresses of normal usage, installation and removal.

The plate member 538 may comprise a flat 534 or rounded top surface or a combination of both. Employing a plate member 538, which is frusto-conical-, bullet-, or dome-like shaped, is also possible. One or more axial grooves 513 may be formed on the edges of the plate member for engaging the projections 508A of an abutment insertion tool such as tool 508 shown in FIG. 14. The axial grooves 513 are preferably arranged to be in axial alignment with the peripherally-disposed, longitudinal grooves 500A in implant 500 or one of the implants of the invention as described herein above. This way, only one set of tools is needed for implant and abutment placement.

Figure 13:
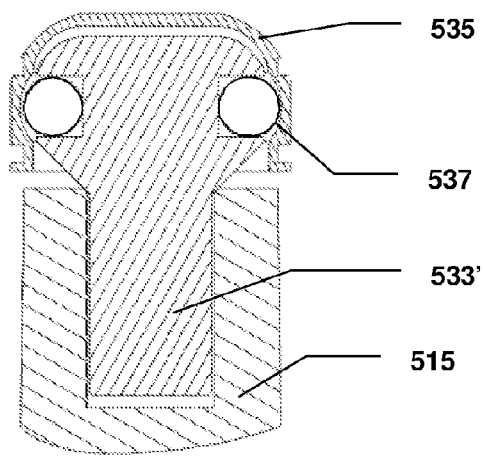
FIG. 13 is a side cut-away elevational view of another O-ring type abutment assembly in an assembled state.
Figure 14:
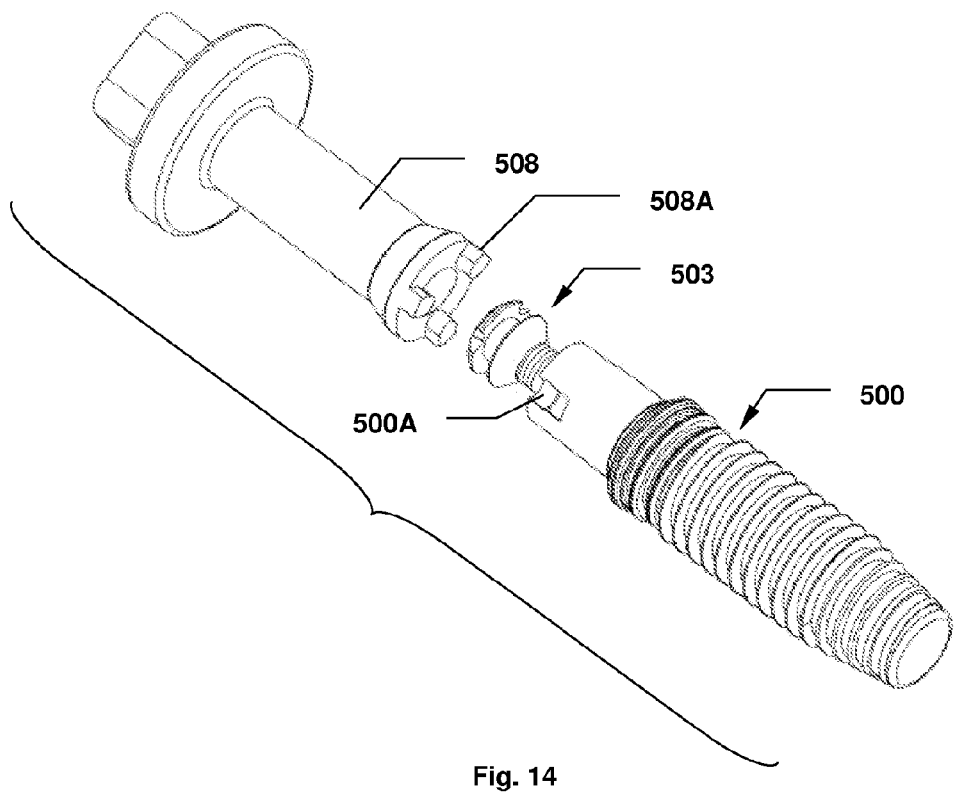
FIG. 14 is a perspective view of an abutment insertion tool and an O-ring abutment attached to a dental implant.

External threads may be provided on the anchoring portion 533 for securing the abutment 503 in the threaded opening of the implant 500 (see FIG. 14). A Morse-type taper connection can also be used. As shown in FIG. 13, the respective male and female taper surfaces of the anchoring portion 533' of the abutment and abutment receiving portion 515 of the implant are sized and configured for mutual taper-locked interconnection.

Figures 12A, 12B:
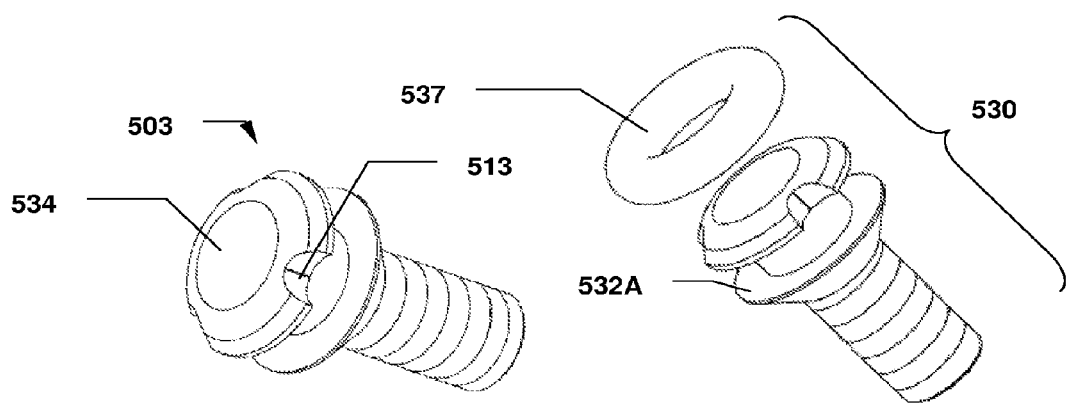
FIG. 12A is a perspective view of an O-ring abutment of the present invention.
FIG. 12B is a perspective view of an O-ring with the O-ring abutment of FIG. 12A.
Figures 12C, 12D:
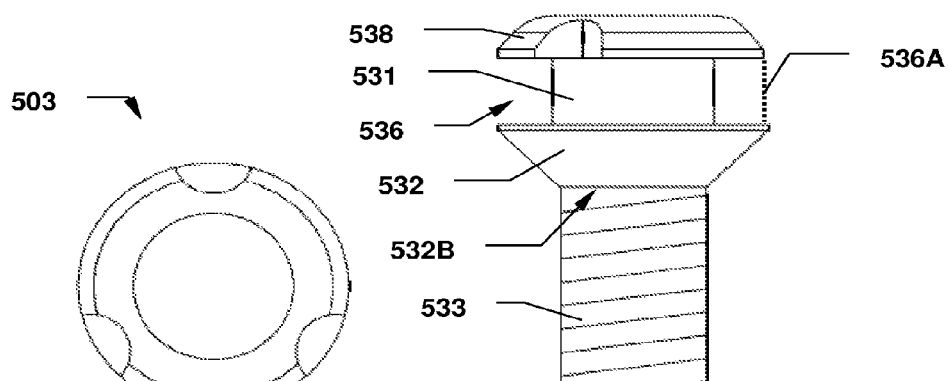
FIG. 12C is a top plan and FIG. 12D is a side elevational view of the O-ring abutment of FIG. 12A.
Figures 12E, 12F:
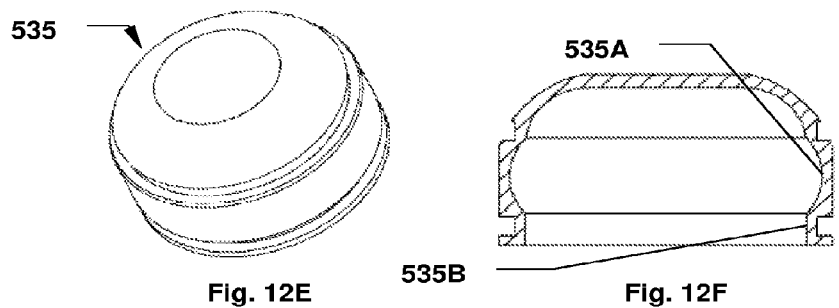
FIG. 12E is a perspective and FIG. 12F is a side cut-away elevational view of a retainer housing for use with the O-ring abutment of FIG. 12A.

As best seen in FIG. 12D and FIG. 13, the seat member 532 tapers to the cross-section of the anchoring portion 533 adjacent the bottom end 532B of the seat member 532, and at least a part of the seat member 532 is depressed into the abutment receiving opening of the implant. The implant preferably comprises a countersunk conical area at an upper region of the abutment receiving opening for receiving a part of the seat member thereon.

In a further embodiment of the abutment assembly 530, the seat member, the anchoring portion and the plate member have an equal, uniform circular cross section, and optionally, the plate member has a rounded top surface.

Improved Impression Coping System

There is a need to accurately transfer position information of the dental implant installed in the patient's mouth to a model used to prepare a dental prosthesis. Thus, it is desirable to have an impression coping suitable for use with the dental implant of the present invention which provides closely matched, complementary mating surfaces to permit precise impression-taking and modeling, despite current manufacturing limitations and tolerances.

Figures 17A, 17B, 17C:
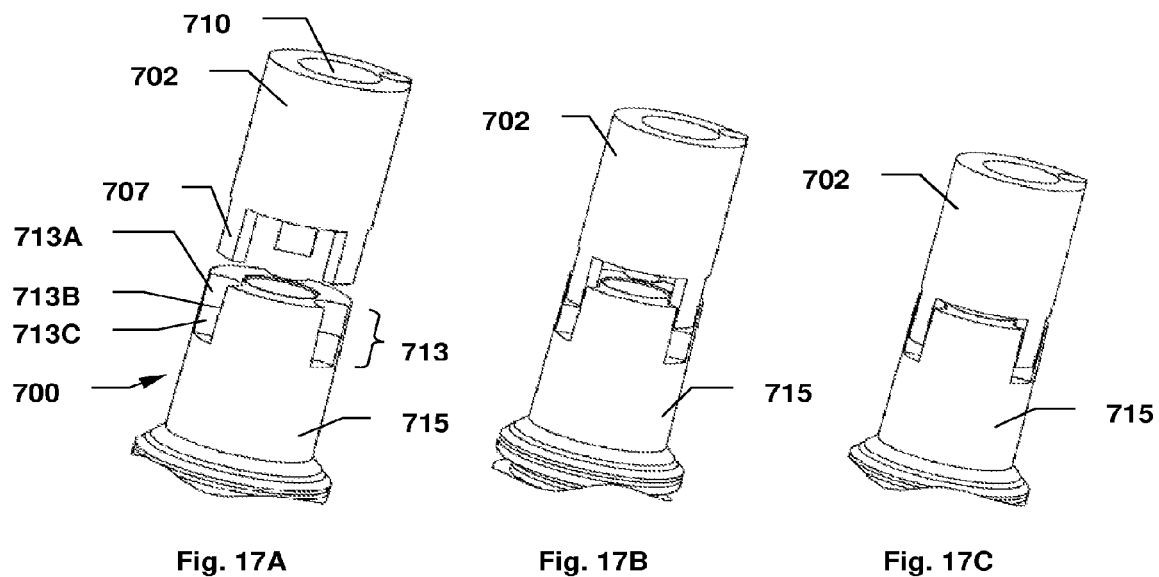
FIGS. 17A to 17C show a perspective view of a device representing a portion of the impression coping or a key of the present invention being brought into engagement with a dental implant.

One preferred impression coping 702 is depicted in FIGS. 17A to 17C, and described as follows. Impression coping 702 has a generally elongated body having spaced apart, axial projections 707 extending outwardly from one end of the body, and a bore 710 extending axially through the body. At least a part of bore 710 can be threaded. The axial projections 707 are preferably provided with sharp edges. The impression coping 702 shares some similarities with the key of the present invention, except that the impression coping 702 does not have a longitudinal protrusion or rail member or a pin receiving opening. The peripheral wall of the impression coping 702 may be provided with grooves, flat surfaces, raised ribs, recesses, apertures or other suitable surface structures to provide anti-rotation while the impression coping 702 is embedded in the impression material. Accurate fit of the impression coping 702 to the implant 700 is achieved by fabricating the longitudinal grooves 713 of the implant 700 with a larger cross section proximal portion 713A, an apical portion 713C having a smaller cross section relative to the proximal portion 713A and a transition portion 713B which tapers between the proximal portion 713A and the apical portion 713C. This allows the axial projections to be inserted into the proximal portion of the longitudinal grooves 713 without experiencing any, or with relatively small, friction force until the axial projections 707 are at the transition portion 713B. The axial projections 707 are fitted into the transition 713B and apical 713C portions of the longitudinal grooves 713 by exerting an axial force on the impression coping 702 using a threaded screw or bolt, thereby forming at least two points of contact between the axial projections 707 and the longitudinal grooves 713. The screw or bolt is threaded into the threaded opening provided in the top surface of the implant 700. It is preferred, although not necessary, that the threaded opening of the implant 700 has a smaller cross section than bore 710 of the impression coping 702. Preferably, the corners of the axial projection 707 become blunt or dig or bite into the walls of the longitudinal grooves 713, and the axial projections 707 are slightly bent, deflected or displaced outward.

It will be appreciated that the structures of the cooperating mating surfaces of the impression coping 702 and the axial projections 707 can be readily implemented in the keys and dental implants of the present invention as described herein.

The axial projections 707 of the impression coping 702 may correspond to longitudinal grooves 713 of the implant 700 in dimension, shape, number and spacing. In a preferred embodiment, the axial projections 707 are essentially square in shape, while the grooves 713 are semicircular. The inward corners of projections 707 are made to passively fit inside the proximal 713A portions and actively engage the 713B and 713C portions. The walls of the proximal 713A and apical 713C portions of the longitudinal grooves 713 can be parallel. Further, at least a section of the walls of the proximal 713A and apical 713C portions of the longitudinal grooves 713 may be formed at an incline. Further, it is possible to preserve the benefits of the invention by having the proximal portion with parallel grooves and the apical portion formed at an incline, omitting the transition portion.

A suggested procedure for obtaining precise translation of the orientation of the dental implant to a model utilizing impression coping 702 is described below. However, it will be apparent to one of ordinary skill in the art that other embodiments are also possible in which various steps are added, combined, modified, substituted, automated or omitted.

The impressing coping 712 is placed over the implant 700 and orientated to engage the corresponding axial projections 707 and longitudinal grooves 713. A fastener (e.g., threaded screw) is used to urge the axial projections 707 and the longitudinal grooves 713 into a closely fitting engagement and to temporarily secure the impression coping 702 to the implant 700.

Impression material is applied over the impression coping 702A and surrounding dentition utilizing, e.g., standard open tray technique.

Once the impression material sets, the fastener is removed, followed by the removal of the impression material from the patient's mouth. The impression coping 702 is picked up by the impression. With the impression coping 702 remaining in the impression material, an implant analog (post) is brought into engagement with the impression coping 702. The distal end of the implant analog is provided with longitudinal grooves which are substantially similar to those provided on the implant 700 and which correspond to and engage with the axial projections 707 of the impression coping 702. A fastener is again used to temporarily secure the impression coping 702 to the implant analog.

Soft model material is poured into the negative impression (formed in the impression material) into the area immediately surrounding the impression coping 702, while the area surrounding the implant analog is filled with the hard material.

The fastener, impression coping 702 and impression material are removed from the implant analog and the hardened model material. The soft model material can be trimmed back from the implant analog to allow the seating of the implant abutment. A soft model material punch can be used to provide the bore of a certain shape to correspond to the shape of the implant abutment. The implant abutment and/or the dental prosthesis can be fabricated on the implant analog.

It will be understood and appreciated that the concept embodied within the mating structures of the impression coping and the implant body described in a preceding section of this application can be readily applied to various types of two-part dental implant systems (e.g., those with an implant abutment and an implant body), whether now known or later developed, to substantially prevent rotation of the abutment when the abutment is seated on the implant body. A typical dental implant utilized in a two-part dental implant system is generally provided with a hexagonal or tri-lobed projection (or a suitable polygonal protrusion) for engaging the correspondingly configured cavity in the abutment. Alternatively, the projection may be formed on the abutment, and the internal cavity formed in the implant. See U.S. Design Pat. D446, 859, issued to Hurson, for an example of this type of dental implant system. To provide an interference fit, which will substantially inhibit relative rotation between the abutment and the implant, the internal cavity is provided with an upper region of a larger cross-section, a lower region of a smaller cross-section relative to the upper region, and a transition region tapering from the upper region to the lower region. The upper region is configured to permit the protrusion to passively mate with the internal cavity. When the lower edge of the projection reaches the transition region, an axial force will be required to fully insert the projection into and engage the internal cavity. The smaller cross-section of the lower region of the internal cavity causes the (axially-extending) edges of the projection to bite into the inner wall of the lower region to form a relatively rotation-free engagement. Alternatively, the transition region can be omitted. In this case the lower region would have inclined surfaces to mate with the projections. Preferably, the relative rotation between the implant and the abutment, or the impression coping and an implant, is reduced to 0 degree. The above-described coupling surfaces, when employed in the implant-mating recess or projection of an impression coping device in conjunction with an implant having complementary mating surfaces, are especially advantageous for procuring highly accurate dental impressions of a patient's mouth and teeth during a dental reconstruction procedure due to the substantially rotationally-inhibited connection that results.

The principles and concepts of the present invention enumerated herein can be readily implemented in an existing or later developed dental implant system that includes an implant body and an abutment coupled together by means of a taper connection and/or a threaded fastener. For example, U.S. Pat. No. 6,726,481 describes various abutments which are attached to the implant body using a threaded connection (e.g., threaded fastener) and a friction-fit connection formed by complementary, tapered mating surfaces. However, these types of abutments cannot be easily removed for repair or replacement. By providing or configuring the upper section of the axial bore of the abutment with internal threads having a diameter larger than the fastener-receiving opening on the implant body, an abutment removal tool, such as the one disclosed in FIG. 9 at reference numeral 206 can be connected to the abutment, and disengage the abutment from the implant body.

It is also contemplated that the present invention includes implant-abutment systems that, in addition to the novel features described herein above, utilize complementary projecting and recessed hex or polygonal (e.g., with 4-8 side walls) surfaces, or keyed surfaces having a suitable irregularly shaped configuration, as indexing means for ensuring accurate placement and orientation of the abutment relative to the implant body. Preferably (although the reverse configuration is also acceptable), the raised keyed surface is formed on the top surface the implant and the corresponding recessed cavity is formed within the abutment.

Open End Healing Abutment

Current implant systems do not allow the record of the implant orientation to be taken while the healing abutment is attached to the implant.

Healing abutments are used to promote the formation of the gum tissue around the implant during the healing stage. Gum tissue attaches to the surface of the healing abutment. Healing abutments are designed to protrude through the gum and are unscrewed after a period of 3-5 months in order to be able to take transfer impression. Attachment between gingival tissue and abutment is disrupted during abutment removal. Once impression of the implant is taken, the healing abutment is screwed back into the implant and remains there until the permanent prosthesis is made. Weaker attachment is formed between the healing abutment and the gum tissue at this time when compared to the original attachment. Removal and reinsertion of the healing abutment quite often requires local anesthesia.

The purpose of the invention is to provide an abutment which allows the transfer impression to be taken without abutment removal. The improved healing abutment preserves the gingival attachment and eliminates the need for injections.

Figure 18:
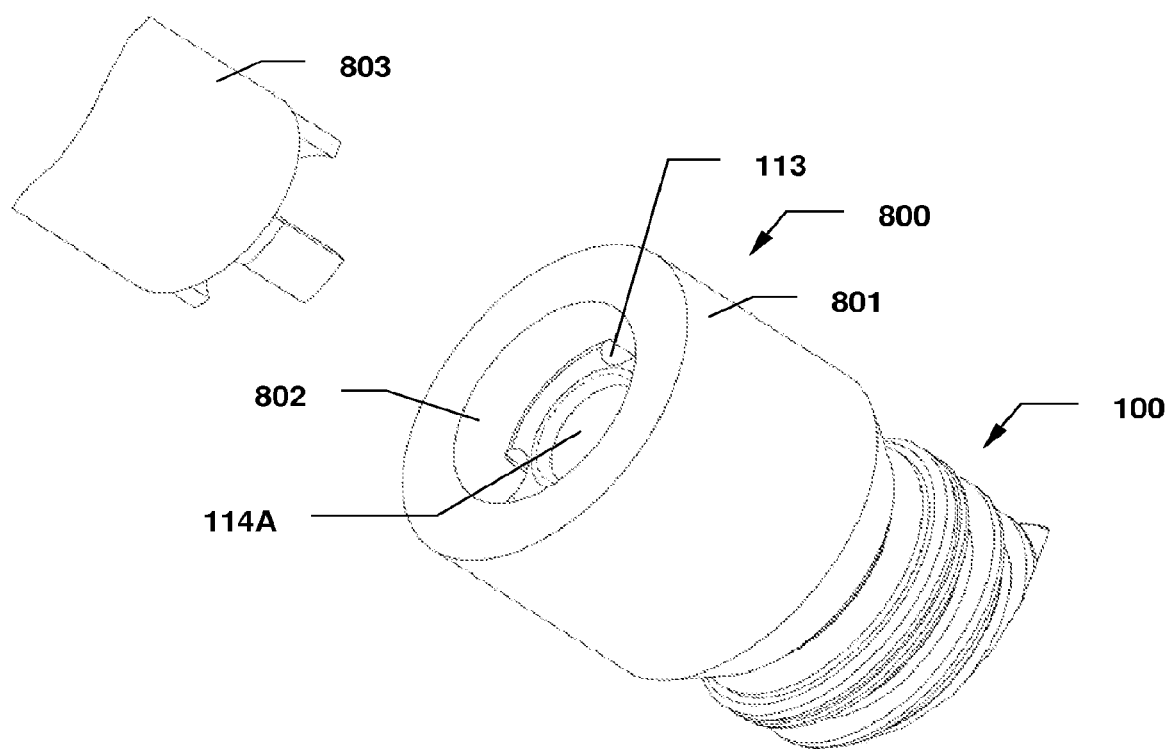
FIG. 18 shows a perspective view of a healing abutment of the present invention.

The healing abutment 800 of the present invention has a peripheral wall 801 and an inside axial bore 802 (FIG. 18). The inside bore 802 has a lower tapered/conical section adapted to form locking taper connection with the implant, and an upper section that has a substantially cylindrical or upwardly and outward flaring inner wall to allow access to the longitudinal grooves 113 of the implant post. The diameter of the upper section is slightly greater than the outside diameter of the impression coping 803, or at least the portion of the impression coping 803 that will be inserted into the upper section. When the healing abutment 800 is installed over the abutment receiving post, the tapered section engages the taper of the post. The tapered section preferably covers only a part of the post length.

In a preferred embodiment, the healing abutment 800 is pressed over the implant post with the abutment placement instrument, similar to the one described above. An implant, or abutment, cover screw is then placed into or over the axial bore 802 to protect internal threaded bore 114A of the abutment receiving post. The outside diameter of the implant cover screw is substantially the same as the inside diameter of the upper section, or it can have a larger diameter to be placed over the healing abutment upper rim.

Coding System

As explained above, the current machining tolerances of 12 microns do not provide sufficient precision when it comes to manufacturing of locking taper components. The 6 micron difference in the diameter of the male component will result in 100 microns of height discrepancy. Generally this will not lead to any complication if the components are attached in the mouth prior to impression taking. The manufactured prosthesis will fit perfectly in this scenario. On the other hand, if the transfer copings are used to record the position of the implants and the implant analogs are used to substitute the implants during the prosthesis making—then the fit of the prosthesis will not be accurate. The reason for this—there is a difference in diameter between implant and implant analog.

It is possible to match each implant with implant analog and to sell them packaged together, but large percentage of dentists do not use implant analogs. Also, if the restoration has to be redone at a later time, it will be impossible to select the appropriate analog.

The system has to be developed to code implants and the analogs according to their diameter or the relevant dimensions. Color coding is a preferred method and can be utilized to code the surface of the implants and implant analogs. The same color can be attributed to the implant and implant analog if they fall within a certain diameter range. Coding can also be done on packaging. Coding of other dimensions, such as locking angle, may also be done. Coding can be utilized in all implant systems which use locking taper or conical connections.

Surgical Screw and Driver

The surgical screw 900 of the present invention has a head 904 and a threaded member 905. The threaded member 905 is placed inside the bone. The head 904 has a centrally located threaded blunt bore 903 at its top end. The peripheral wall of the head has recesses 902 to mate with the protrusions 906 of the screw placement instrument 910. The screw placement instrument 910 is similar to the implant placement instrument described above. The protrusions 906 can be surrounded by an annular collar 907, if desired or necessary, to provide more rigidity.

Fastener of the screw placement instrument engages the threaded blunt bore 903 of the surgical screw 900. Prongs 906 of the screw placement instrument 910 engage the recessed areas 902. It will be appreciated that the screw placement instrument 910 and the surgical screw 900 can be designed to have complementary engaging components or surfaces of different number, shape, size, orientation and location.

While specific embodiments of the invention have been shown and described in detail to illustrate the application of the principles of the invention, it will be understood that the invention may be embodied otherwise without departing from such principles.

What is claimed is:

1. A method of attaching an implant abutment to a dental implant, comprising the steps of:
    providing an implant abutment having a peripheral wall and a substantially central axial bore extending through the abutment, the substantially central axial bore having a lower part, a central threaded bore part, and an upper part, the lower part of the substantially central axial bore having a conical interior wall adapted to form a locking taper connection with the abutment receiving portion of the implant;
    providing a dental implant, the dental implant comprising an apical end, a top end, and an anchoring portion adjacent the apical end, the anchoring portion being adapted to engage bone and having an axial length, the dental implant being provided with an internally threaded opening of a predetermined depth accessible from the top end of the dental implant, an abutment receiving portion adjacent the top end of the dental implant for receiving the abutment, the abutment receiving portion being provided with at least one longitudinal groove of a selected shape extending downwardly a predetermined length from the top end of the dental implant, the abutment receiving portion being tapered toward the top end;
    providing an annular shoulder formed between the anchoring portion and the abutment receiving portion;
    providing an insertion tool that engages the internal threaded bore of the implant; and
    applying an axial seating force to the implant abutment by screwing the insertion tool into the internal threaded bore; and
    urging the implant abutment and the implant together to form a locking taper connection;
    removing the insertion tool by unscrewing the insertion tool from the internal threaded bore; and
    after removal of the insertion tool, cementing a crown over the implant abutment.

2. The method of claim 1, further comprising the step of removing the abutment by engaging the central threaded bore part of the abutment with an abutment removal tool and applying an axial force.

3. The method of claim 1, wherein a rotation of the abutment insertion tool is accomplished with a torque applying tool.

4. The method of claim 3, wherein the torque-applying tool is a torque wrench.

* * * * *